(12) United States Patent
Uyeda et al.

(10) Patent No.: US 7,361,516 B2
(45) Date of Patent: Apr. 22, 2008

(54) FIELD OF MODULAR MULTIFUNCTIONAL LIGANDS

(75) Inventors: Harry T. Uyeda, College Park, MD (US); Hedi Mattoussi, Alexandria, VA (US); Igor L. Medintz, Alexandria, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/956,586

(22) Filed: Sep. 24, 2004

(65) Prior Publication Data

US 2006/0068506 A1 Mar. 30, 2006

(51) Int. Cl.
*G01N 33/544* (2006.01)
*G01N 33/551* (2006.01)
*C07C 321/112* (2006.01)
*C07C 321/116* (2006.01)

(52) U.S. Cl. ...................... 436/528; 436/525; 436/120; 530/404; 530/406; 568/25; 568/67; 568/75

(58) Field of Classification Search ................ 436/524, 436/525, 528, 120; 530/404, 406; 554/227; 459/35; 568/25, 67, 75
See application file for complete search history.

(56) References Cited

U.S. PATENT DOCUMENTS

| | | | |
|---|---|---|---|
| 6,251,303 | B1 | 6/2001 | Bawendi et al. |
| 6,426,513 | B1 | 7/2002 | Bawendi et al. |
| 2001/0023078 | A1* | 9/2001 | Bawendi et al. ............ 436/524 |
| 2002/0025312 | A1* | 2/2002 | Tagawa et al. ........... 424/130.1 |
| 2002/0182632 | A1 | 12/2002 | Anderson et al. |
| 2003/0059865 | A1* | 3/2003 | Nelson ........................ 435/25 |

OTHER PUBLICATIONS

Griffin et al. Specific covalent labeling of recombinant protein molecules inside live cells. Science 1998, vol. 281, pp. 269-272.*

(Continued)

*Primary Examiner*—Long V. Le
*Assistant Examiner*—Shafiqul Haq
(74) *Attorney, Agent, or Firm*—John J. Karasek; Joseph T. Grunkemeyer

(57) ABSTRACT

This invention pertains to a surface ligand; preparation of the ligand; colloidal nanoparticle, such as quantum dot bearing one or more of the ligand; and a bioconjugate characterized by a nanoparticle bearing one or more of the ligand conjugated to a biomolecule. The ligand is characterized by the presence of a first module containing atoms that can attach to an inorganic surface; a second module that imparts water-solubility to the ligand and to the inorganic surface that may be attached to the ligand; and a third module that contains a functional group that can, directly or indirectly, conjugate to a biomolecule. Order of the modules can be different and other modules and groups can be on the ligand. Preparation of the ligand includes the steps of reacting a compound having atoms that can attach to an inorganic surface with a water-solubilizing compound that imparts the property of water-solubility to the ligand and the inorganic surface to which it may be attached and purification thereof. Colloidal nanoparticle is characterized by an inorganic surface having attached to it one or more of the ligands, The colloidal bioconjugate is characterized by an inorganic surface having attached thereto one or more of the ligand wherein at least some of the ligand have a biomolecule conjugated thereto.

8 Claims, 3 Drawing Sheets

OTHER PUBLICATIONS

Bandyopadhyay et al. Self-assembled monolayers of bis-thioctic ester derivatives of oligoethyleneglycols: remarkable selectivity for K+/Na+ recognition. Chem. Commun. 2000, pp. 141-142.*

Bandyopadhyay et al. Ion recognition at the interface of self-assembled monolayer(SAMs) of bis-thioctic ester derivatives of oligo (ethyleneglycols). Chem. Eur. J 2000, vol. 6, No. 23, pp. 4385-4392.*

Herranz et al. Metal ion recognition and molecular templating in self-asembled monolayers of cyclic and acyclic polyethers. PNAS 2002, vol. 99, No. 8, pp. 5040-5047.*

Segura et al. New concepts in tetrathiafuvalence chemistry. Angew. Chem. Int. Ed. 2001, vol. 40, pp. 1372-1409.*

Mattoussi et al., "Self-Assembly of CdSe-ZnS Quantum Dot Bioconjugates Using an Engineered Recombinant Protein" J. Am. Chem. Soc., 122(49), 12142-12150 (2000).

* cited by examiner

| 1 | 2 | 3 |
FIG. 1
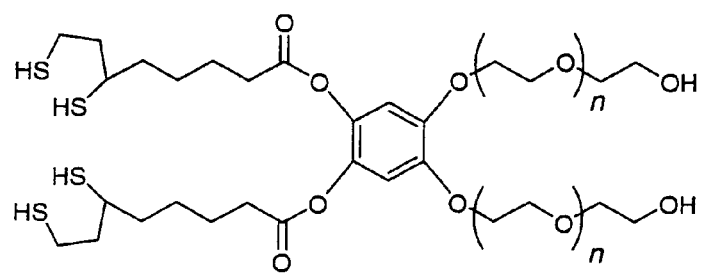
FIG. 2
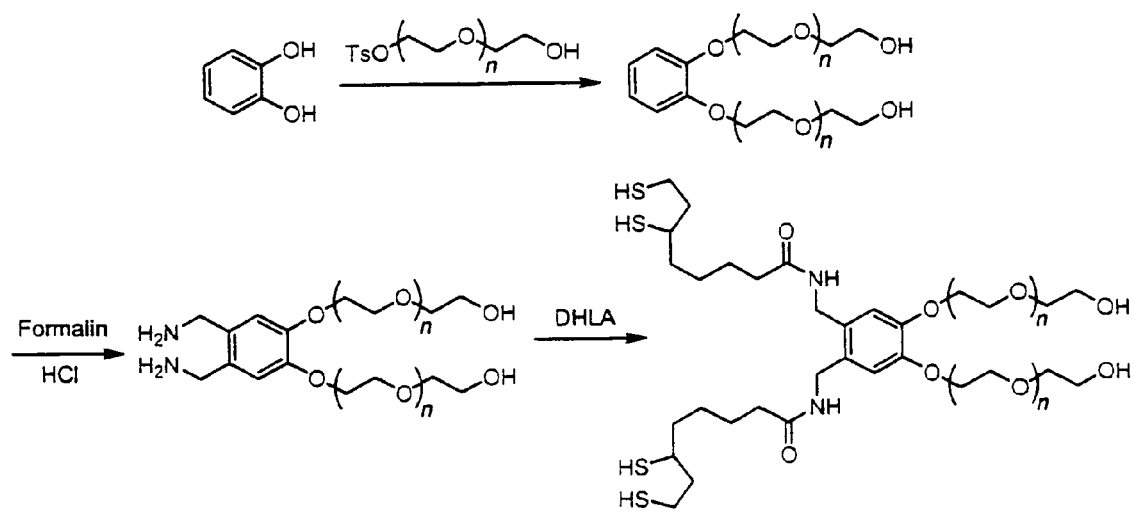
FIG. 3

FIELD OF MODULAR MULTIFUNCTIONAL LIGANDS

BACKGROUND OF THE INVENTION

1. Field of the Invention

This invention pertains to the field of multifunctional ligands, colloidal nanoparticles and colloidal bioconjugates.

2. Description of Related Prior Art

Known methods to prepare water-soluble nanoparticles, such as semiconductor nanoparticles (quantum dots) and matallic nanoparticles, involve the capping of those nanoparticles with ionized dihydrolipoic acid molecules. Electrostatic self-assembly techniques allow one to easily prepare bioconjugates that take advantage of positively charged domains of proteins coupled to the negatively charged carboxylate groups on the nanoparticle surface. Some limitations to this approach include the restriction of operating in basic environments and the inability to form direct covalently linked nanocrystal-biomolecule conjugates.

Other known approaches have used small organic surface ligands, such as mercaptoacetic acid and aminoethane thiol, to generate water-soluble nanoparticles and other systems. The major disadvantage of such systems involves the poor temporal stability of the nanoparticle ligands due to the nature of the singly bound water-solubilizing groups which results in aggregated solutions after a short time. Water solubilization of nanoparticles with hydrophilic dendritic structures and layer-by-layer assembly techniques has also been demonstrated with some degree of success. Most of these strategies provide for any pH stability, let alone long-term water solubility.

OBJECTS AND BRIEF SUMMARY OF THE INVENTION

An object of this invention is a multifunctional ligand with two or more thiol or other groups for attaching to an inorganic particle, such as a quantum dot, the ligand being characterized by the presence of attaching, water-solubilizing and functional groups.

Another object of this invention is preparation of the ligand.

Another object of this invention is a quantum dot having attached to its surface at least one of the ligands.

Another object of this invention is a ligand having attached thereto a bioconjugate, such as a DNA or another biomolecule.

Another object of this invention is a water-soluble semiconducting nanoparticle having attached thereto at least one ligand that is conjugated to a biomolecule.

Another object of this invention is a water-soluble semiconducting nanoparticle having unique properties of wide pH stability, the ability to remain luminescent in basic and acidic solutions and being aggregate-free over extended period of time measured in terms of months.

These and other objects can be attained by a ligand that is characterized by a polar head that contains at least two attaching atoms: a hydrophilic moiety that can impart water-solubility to inorganic nanoparticle that the ligand is attached to, and a functional group to which a biomolecule can be attached.

BRIEF DESCRIPTION OF THE DRAWINGS

FIG. 1 is a schematic representation of the multifunctional ligand having at least two attaching atoms, a water-solubilizing group and a functional group that can be conjugated, directly or indirectly, to a biomolecule.

FIG. 2 is a structural formula of a multifunctional ligand having four attaching thiol groups in a broken two five-member rings.

FIG. 3 shows structural formulas of ingredients used in the proposed synthesis of a typical multi-dentate ligand made of dihydrolipoic acid fused with a polyethylene glycol.

DETAILED DESCRIPTION OF THE INVENTION

Figure 4:
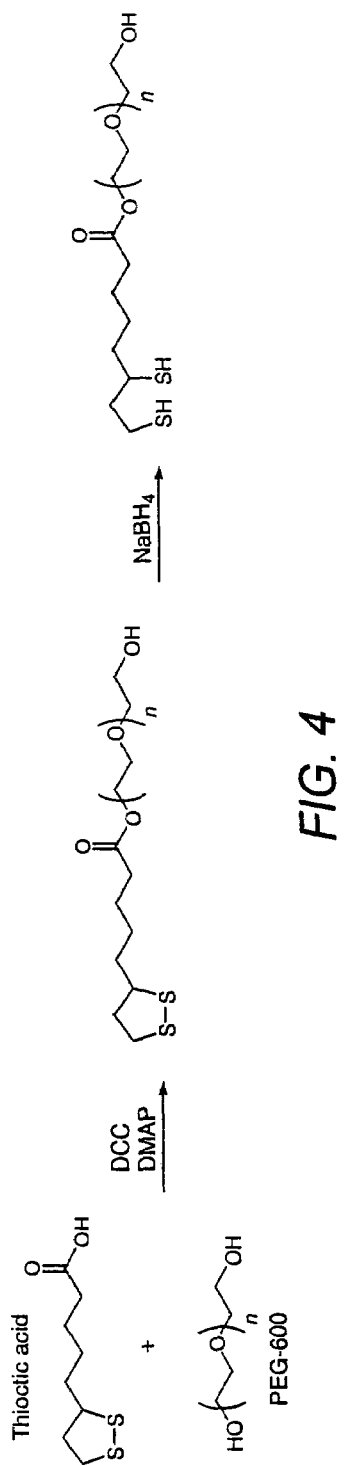
FIG. 4 is a representation of the synthesis of a ligand which is prepared by coupling thioctic acid and poly(ethylene glycol) of 600 molecular weight, used in example, followed by opening of the ring.

This invention pertains to novel surface ligands, preparation of the ligands, colloidal nanoparticles and colloidal bioconjugates to arrive at water-soluble semiconducting nanoparticles through the use of one or more surface ligands that may be conjugated to additional compounds, especially biomolecules. The invention is characterized by the use of specific ligands that are attached to nanoparticles and impart water-solubility and numerous other functions. These ligand agents are chosen from groups consisting of multi-dentate or tooth-like thiol based or other complexing agents that bear hydroxy-terminated poly(ethylene glycol) or other hydrophilic groups of varying lengths. Such surface ligands can also be modified with amino, carboxylic acid and other functionalities, thus extending their usefulness in more elaborate conjugation schemes. Mixtures of these functionalized and unfunctionalized ligands can be further employed to design and prepare more highly structured systems in the coupling of nanoparticles to biomolecules. The chain length of the poly(ethylene glycol) unit and other hydrophilic moieties can be tailored to further tune the solubility of the nanoparticle-ligand complex in both organic and aqueous environments. Furthermore, branched water-soluble complexes may provide ligands with three or more functionalities that will be imparted to each nanoparticle. Among the unique characteristics imparted to the nanoparticles by these novel ligands are a wide pH stability range, the ability to remain luminescent in basic buffer solutions and remain aggregate-free over extended periods of time in terms of months. Uses for the described invention include the use of nanoparticle-conjugates in biosensing, bioimaging and other biooriented applications.

More specifically, this invention pertains to ligands containing at least two thiol groups that attach to an inorganic surface, method for preparing the ligands by coupling a ring di-thiol acid and a polyethylene glycol, colloidal quantum dots and quantum ddot bioconjugates.

Advantages of the herein described and claimed invention include the following: broad acidic and basic pH stability of the colloidal nanoparticles and colloidal bioconjugates: non-toxicity in and/or to living cells of the colloidal nanoparticles and colloidal bioconjugates; non-aggregation in living cells of the colloidal nanoparticles and colloidal bioconjugates; covalent conjugation of the ligand to biomolecules; and control of biomolecular conjugation quantity, particularly when using mixed ligands.

Referring to FIG. 1, the ligand includes module #1, which includes a group for attaching to an inorganic surface; module #2, which includes a water-solubilizing group that imparts water solubility and pH stability to the colloidal nanoparticle and colloidal bioconjugate; and module # 3, which includes a functional group that allows conjugation to a biomolecule, directly or indirectly. It should be understood that the ligand can have more than three modules and module order can be different in that module #3 can be positioned before module #2 and it need not be positioned at end of the ligand.

The surface interactive group or the attaching group of module #1 can be any chemical moiety having elements or chemical groups contained therein that are capable of binding to the surface of the inorganic particle. For example, the surface group includes, but is not limited to one or more SH, $NH_2$, P, O or O=P. The attaching group of module #1 can contain passive components, such as alkylene groups, that do not apparently contribute to the function of the attaching group. A typical example of a suitable compound that contains an alkylene group is an open thioctic acid which is composed of a five member ring containing two thiol atoms, a passive —$CH_2$ $CH_2$— alkylene group attached to a carboxyl-COOH end group. More than two thiol groups can be present in the acid, such as in the ligand whose structural formula is shown in FIG. 2. In preparation of the ligand of FIG. 3, resorcinol is coupled to a mono tosylated oligo (ethylene glycol) in a Mitsunobu ether synthesis. The resulting 1,2-bis-oligo(ethylene glycol)benzene is modified in the Gabriel synthesis to give the diamino species upon reaction with formalin and hydrochloric acid. Amide formation of the amines and the carboxylic acid of dihydrolipoic acid then results in the desired multi-dentate capping ligand shown in FIG. 3, where the repeating group "n" is typically in the range of 3-100, more typically 4-10.

The functional end group of module #3 can be provided by the reaction of an acid with a poly(ethylene glycol) or a polysacchride, such as dextrin. The functional group can be modified by known techniques. Ligands have been prepared with functional groups and groups that include carboxylic, thiol, aryl and hydroxy groups that can be used in the conjugation to proteins, DNA, RNA and other biologically relevant groups.

The water solubilizing modular group of the designed ligand is based upon well-established amphiphilic biocompatible poly(ethylene glycol) units. Because there is a wide variety of inexpensive, commercially available poly(ethylene glycols), enormous tailorability exists to modify the solubility of the composite system. Furthermore, the modular nature of the poly(ethylene glycol) groups can be tailored to include cross-linkable subunits that can polymerize in the nanoparticle-ligand complex to form a core-protected encapsulated species that effectively shields it from the environment, a highly desirable trait for colloidal quantum dots, for example, in order to completely passivate the surface and ensure a high photoluminescence efficiency.

Typical preparation of a ligand is illustrated in FIG. 4 and involves the reaction of an acid and a poly(ethylene glycol). In a typical synthesis, commercially available thioctic acid and a 600 average molecular weight poly(ethylene glycol) are coupled in the presence of dicyclohexylcarbodiimide (DCC) and 4-dimethylamino-pyridine (DMAP) in dichloromethane (DM) for several hours. Purification of the ligand can be achieved by column chromatography on silica gel utilizing a mobile phase consisting of chloroform, methanol and acetone. The dithiane ring system of the material was reduced to the ring-opened dithiol in the presence of sodium borohydride ($NaBH_4$) at room temperature. Purification of the ligand was achieved through the use of silica gel chromatography and similar mobile phase. Characterization of the ligand poly(ethylene glycol) and dihydrolipoic acid, i.e., opened thioctic acid, was achieved through $^1$H-NMR and $^{13}$C-NMR spectroscopy. Identification of the proposed species was determined by comparison to the parent subunits. Integration ratios of the poly(ethylene glycol) resonances to the dihydrolipoic acid based resonances also confirmed the approximate chain length of the poly(ethylene glycol).

It should be noted that FIG. 4 depicts a reaction wherein the poly(ethylene glycol) is attached to the acid first and then the ring with the two thiol atoms is opened, thus separating the thiol groups. It is also possible to first open the ring and then attach the poly(ethylene glycol). However, attachment and subsequent ring opening, shown in FIG. 4 is preferred since yield of the ligand is typically increased from about 30% to about 80% and purification thereof is much cleaner. However, a group can be provided in a known way at end of the ligand of FIG. 4 which can directly conjugate to a biomolecule.

A colloidal nanoparticle is an inorganic nanoparticle attached to at least one ligand. In general, the inorganic particle can be any inorganic material exhibiting a distinct physical property that can be used to identify that material. The physical properties can be, but are not limited to, emission such as photoluminescence, absorption, scattering and plasmon resonances. For example, the inorganic particle can be illuminated with a light source at an absorption wavelength to cause an emission at an emission wavelength that can be used to distinguich the emitting material from other materials.

Examples of inorganic particles include, but are not limited to, inorganic colloids and semiconducting nanoparticles. The particles can be metallic or magnetic. The particles can also be crystalline. Examples of inorganic colloids include Ag, Au or a phosphor. The phosphor can be an inorganic phosphor, such as a rare earth oxide. The inorganic colloids can exhibit distinct reflectivity and scattering properties, depending on the size of the particles in the colloid. Examples of semiconducting nanoparticles include compounds of groups II-VI, III-V and IV of the Periodic Table. Elements from these groups include binary CdS, CdSe, CdTe, ZnS, ZnSe, ZnTe, MgTe, GaAs, GaP, GaSb, GaN, HgS, HgSe, HgTe, InAs, InP, InSb, InN, AlAs, AlP, AlSb, AlS, PbS, PbSe, Ge, Si, or an alloy or a mixture thereof, including ternary and quaternary mixtures. The semiconducting nanoparticles can be semiconducting nanocrystals or quantum dots. The nanocrystals can be illuminated with a light source at an absorption wavelength to cause an emission at a different wavelength. The emission has a frequency that corresponds to a band gap of quantum confined semiconductor material. The band gap is a function of the size of the nanocrystal. Nanocrystals having small diameters can have properties intermediate between molecular and bulk forms of matter. For example, nanocrystals based on semiconductor materials having small diameters can exhibit quantum confinement of both the electron and hole in all three dimensions, which leads to an increase in the effective band gap of the material with decreasing crystallite size. Consequently, both the optical absorption and emission of nanocrystals shift to the blue, i.e., to higher energies, as the size of the crystallites decreases. Of particular interest herein is the use of the nanoparticles, such as quantum dots, having thereon one or more ligands. Quantum dots having one or more ligands attached thereto are referred to herein as colloidal quantum dots, indicating the ability to disperse them in solution, such as organic and aqueous environments.

The outer surface of the nanocrystal can include a layer of compounds derived from the coordinating solvent used during the growth process. The surface can be modified by repeated exposure to an excess of a competing coordinating group to remove the native ligand and replace it with the new one. For example, a dispersion of the capped nanocrystal can be treated with a coordinating organic compound, such as pyridine, to produce crystallites which disperse readily in pyridine, methanol, and aromatics but no longer disperse in aliphatic solvents. Such a surface exchange process can be carried out with any compound capable of coordinating to or bonding with the outer surface of the nanocrystal, including, for example, phosphines, thiols, amines and phosphates. The nanocrystal can be exposed to short chain polymers which exhibit an affinity for the surface and which terminate in a moiety having an affinity for a suspension or dispersion medium. Such affinity improves the stability of the suspension and discourages flocculation of the nanocrystal.

Pursuant to prior art practice, nanoparticle size distribution during the growth stage can be estimated by monitoring the absorption line widths of the particles. Modification of the reaction temperature in response to changes in the absorption spectrum or emission spectrum of the particles allows the maintenance of a sharp particle size distribution during growth. Reactants can be added to the nucleation solution during crystal growth to grow larger crystals. By stopping growth at a particular nanocrystal average diameter and choosing the proper composition of the semiconducting material, the emission spectra of the nanocrystals can be tuned continuously over the wavelength range of 400 to 800 nm. The nanocrystal has a diameter of less than 150 Å. A population of nanocrystals has average diameters in the range of 15 Å to 125 Å. In a quantum dot, the core is typically in the range of 15-125 Å, more typically 20-40 Å, and the coating thickness is typically in the range of 2-100 Å, more typically 5-30 Å.

Transmission electron microscopy or small angle x-ray scattering can provide information about the size, shape and distribution of the nanocrystal population. Powder x-ray diffraction patterns can provide the most complete information regarding the type and quality of the crystal structure of the nanocrystals. Estimates of size are also possible since particle diameter is inversely related, via the x-ray coherence length, to the peak width. For example, the diameter of the nanocrystal can be measured directly by transmission electron microscopy or estimated from x-ray diffraction data using, for example, the Scherer equation. It also can be estimated from the UV/Vis absorption spectrum.

Preparation of the quantum dots bearing water-soluble dihydrolipoate-poly(ethylene glycol) ligands can be accomplished in several steps. Typically, a small volume of the quantum dot solution in the native trioctylphosphine/trioctylphosphine oxide is precipitated with methanol and centrifuged to remove the excess trioctyphosphine- and phosphineoxide. An excess of the poly(ethylene glycol) modified dihydrolipoic acid is added (either neat of in methanol or ethanol) to the precipitated quantum dots and the system is evacuated and backfilled with an atmosphere of nitrogen. The quantum dots readily disperse in the neat ligand (or a solution containing the ligand) with gentle heating and the solution is allowed to stir for several hours. The solution is then further diluted with a small volume of ethanol and precipitated with hexanes and chloroform to ensure a monophasic solution in which the quantum dots are precipitated. The precipitate is concentrated by centrifuging and the supernatant is discarded. The process is repeated 2 to 3 times and the sample is then dried under a gentle stream of nitrogen. The quantum dots are dispersed in water and purified through a centrifugal filtration device with a nominal molecular weight cutoff at 50,000 and filtered through a 0.45 μm PTFE frit. The water soluble quantum dots are then transferred to aqueous buffer solutions at various pHs and remain aggregate-free for extended periods of time of many months.

Figure 5:
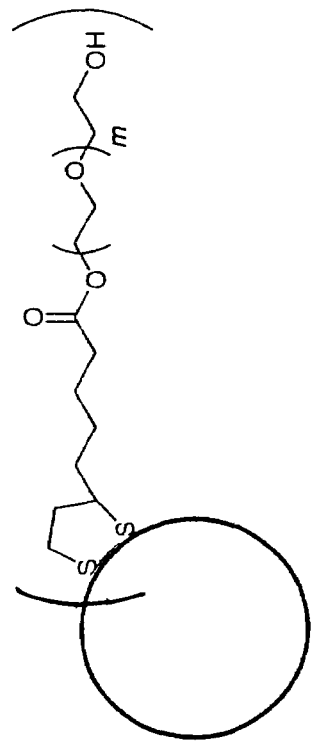
FIG. 5 is a representation of an inorganic colloidal quantum dot with one dihydrolipoic acid-polyethylene glycol ligand attached to its surface.

FIG. 5 is a depiction of a colloidal quantum dot CdSe/ZnS wherein m is 6, indicating 6 separating poly(ethylene oxide) repeating units. It should be understood that the colloidal quantum dot of FIG. 5 can bear many, i.e., hundreds and thousands, of the surface ligands. Also, m can be larger than 6.

Figure 6:
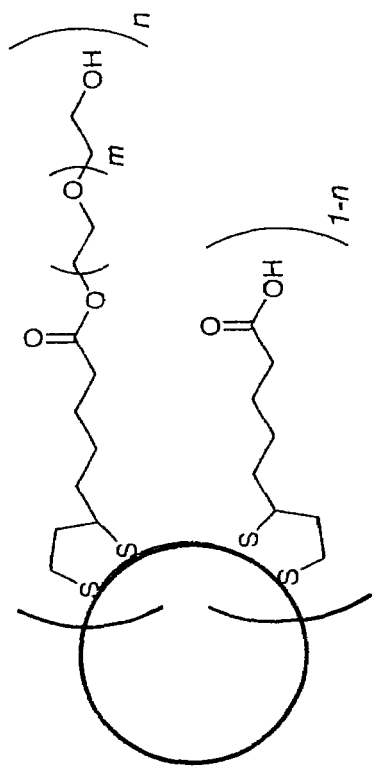
FIG. 6 is a representation of a mixed colloidal quantum dot with two ligands attached to its surface, one of the ligands showing a functional group (-COON) that can be used for further chemical coupling to directly conjugate to a biomolecule.

FIG. 6 shows a mixed surface ligand composition of dihydrolipoic acid to dihydrolipoic acid-poly(ethylene glycol) 600 (PEG) on the quantum dot. Aqueous solutions with ratios using 1:0 to 0:1 of dihydrolipoic acid (DHLA) to DHLA-PEG (600) surface ligands were prepared.

Figure 7:
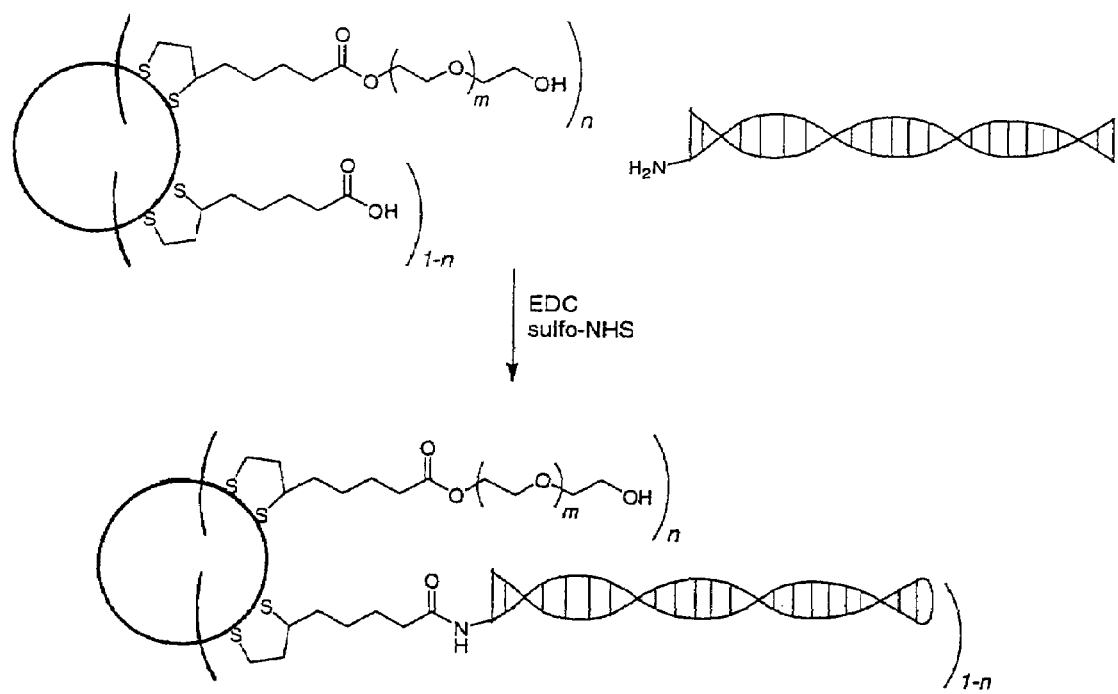
FIG. 7 is schematic representation of conjugating a biomolecule to a colloidal nanoparticle having mixed surface ligands.

FIG. 7 schematically depicts a reaction of a mixed ligand colloidal quantum dot with a DNA biomolecule in presence of ethylene 1-ethyl-3-(3-dimethylaminopropyl) carbodiimide hydrochloride (EDC) and N-hydroxysulfosuccinimide (sulfo-NHS). Duration of the biomolecule DNA conjugation is typically 10-30 minutes and it can be carried out at room temperature.

Figure 8:
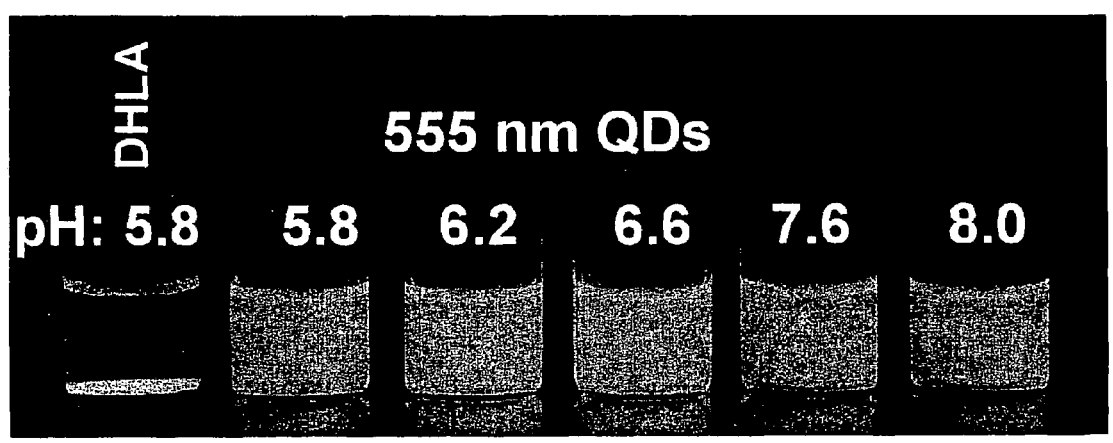
FIG. 8 shows a luminescence image set of 545mn-emitting CdSe-ZnS quantum dots in phosphate buffer saline solution at various pH values after 2 days at room temperature with vial (1) quantum dots coated with the closed ring compound "E" shown in FIG. 4, where n is about 21, at pH of 5.8; and vials 2-6 quantum dots coated with the open ring compound "F" shown in FIG. 4, where n is about 12 at pH 5.8, 6.2, 6.6, 7.6, and 8.0, respectively.

FIG. 8 shows a luminescence image of sets of two solutions of quantum dots capped with the dihydrolipoic acid-polyethylene glycol (600) of this invention at various pHs compared to solution of quantum dots capped with a prior art compound.

The pH variation is based on experiments of incubating the quantum dots coated with poly(ethylene glycol)-modified dihydrolipoic acid ligands at pHs of 5 to 8, which suggests that luminescence of such systems are quite stable and unaltered from prior art. Luminescence experiments were conducted with CdSe/ZnS quantum dots coated with DHLA-PEG (600) in buffered aqueous solutions. The samples were excited with a UV lamp at 365 nm and the emission was centered at 553 nm. The use of mixed ligand strategy is not limited to dihydrolipoic acid, since others can be used.

In practice, the mixed surface ligand is typically used since the group (—COOH) can be directly conjugated to a biomolecule. The mixed ligand approach is also typically used since it allows for better control of the quantity of the biomolecule that can be provided on an inorganic surface of nanoparticles or quantum dots. Advantages of using mixed surface ligands include control of functional groups on the nanoparticle; makes solubility and coupling to biomolecules two separate issues; allows one to use a multiple of functional groups without affecting solubility; and allows one to titrate down the number of coupled molecules to 3, 2, or even 1.

What is claimed is:

1. A ligand comprising
A first module comprising:
two 1,3-dimercaptopropyl groups that can attach to an inorganic surface;
an alkylene moiety attached to each of the 1,3-dimercaptopropyl group; and
a bridging group having the formula

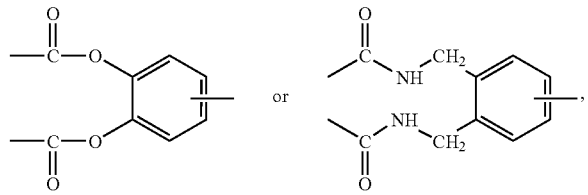

wherein each of the ester or the amide moiety of the bridging group is linked to each of the alkylene moiety attached to 1,3-dimercaptopropyl group;
two second modules attached to the bridging group that can impart water-solubility to said ligand and to said inorganic surface to which said ligand may be attached and wherein the bond to the right of the phenyl ring shows point of attachment to the second modules; and
a third module that contains a functional group;
wherein the second module is positioned between the first module and the third module.

2. The ligand of claim 1 wherein said functional group is selected from the group consisting of hydroxyl, carboxyl, amino, aryl, and sulfhydryl groups.

3. The ligand of claim 2 wherein said second module includes water-solubilizing repeating units of compounds selected from the group consisting of poly(ethylene glycol), polysaccharides, and mixtures thereof.

4. The ligand of claim 3 wherein the number of said repeating units derived from poly(ethylene glycol) is from about 3 to about 100.

5. The ligand of claim 1 wherein the alkylene moiety has 2 to 4 carbon atoms and is attached to the ester group;
said second module consists of one or more ethylene oxide repeating units derived from poly(ethylene glycol); and
said functional group in said third module is a hydroxyl group.

6. The ligand of claim 3 wherein the alkylene moiety has 2 to 4 carbon atoms and is attached to the ester group;
said second module consists of 4 to 10 ethylene oxide repeating units derived from poly(ethylene glycol); and
said functional group of said third module is carboxyl group.

7. The ligand of claim 1, wherein the ligand is:

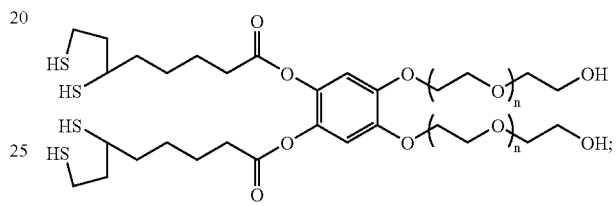

wherein each n is an integer from 3 to 100.

8. The ligand of claim 1, wherein the ligand is:

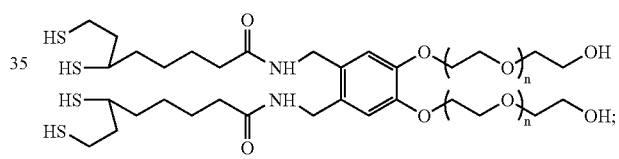

wherein each n is an integer from 3 to 100.

* * * * *